US007126005B2

(12) United States Patent
Handa et al.

(10) Patent No.: US 7,126,005 B2

(45) Date of Patent: Oct. 24, 2006

(54) PROCESS FOR PREPARING FLORFENICOL

(75) Inventors: Vijay Kumar Handa, Banjara Hills (IN); Arun Kumar Gupta, Kukatpally (IN); Meenakshisunderam Sivakumaran, Somajiguda (IN)

(73) Assignee: Aurobindo Pharma Limited, Ameerpet Hyderabad (IN)

(*) Notice: Subject to any disclaimer, the term of this patent is extended or adjusted under 35 U.S.C. 154(b) by 421 days.

(21) Appl. No.: 10/735,892

(22) Filed: Dec. 16, 2003

(65) Prior Publication Data

US 2005/0075506 A1 Apr. 7, 2005

(30) Foreign Application Priority Data

Oct. 6, 2003 (IN) .......................... 806/CHE/2003

(51) Int. Cl.
*C07D 263/04* (2006.01)
*C07C 313/04* (2006.01)

(52) U.S. Cl. ........................................ 548/215; 558/61

(58) Field of Classification Search ................ 548/215; 558/61

See application file for complete search history.

(56) References Cited

U.S. PATENT DOCUMENTS

| | | | | |
|---|---|---|---|---|
| 2,757,209 | A | 7/1956 | Joris | 260/621 |
| 2,759,927 | A | 8/1956 | Suter | 260/239 |
| 2,759,970 | A | 8/1956 | Suter | 260/562 |
| 2,759,971 | A | 8/1956 | Cutler | 260/562 |
| 2,759,972 | A | 8/1956 | Suter | 260/562 |
| 2,759,976 | A | 8/1956 | Suter | 260/570.5 |
| 4,235,892 | A | 11/1980 | Nagabhushan | 424/226 |
| 4,311,857 | A | 1/1982 | Nagabhushan | 564/212 |
| 4,361,557 | A | 11/1982 | Nagabhushan | 424/226 |
| 4,582,918 | A | 4/1986 | Nagabhushan | 549/551 |
| 4,677,214 | A | 6/1987 | Nagabhushan | 549/551 |
| 4,743,700 | A | 5/1988 | Jommi et al. | 548/216 |
| 4,876,352 | A | 10/1989 | Schumacher et al. | 549/232 |
| 4,973,750 | A | 11/1990 | Nagabhushan | 564/135 |
| 5,082,863 | A | 1/1992 | Apelian et al. | 548/216 |
| 5,105,009 | A | 4/1992 | Jommi et al. | 564/135 |
| 5,153,328 | A | 10/1992 | Jommi et al. | 548/239 |
| 5,202,484 | A | 4/1993 | Villa et al. | 546/302 |
| 5,227,494 | A | 7/1993 | Schumacher et al. | 548/237 |
| 5,243,056 | A | 9/1993 | Jommi et al. | 548/232 |
| 5,284,966 | A | 2/1994 | Villa et al. | 560/9 |
| 5,332,835 | A | 7/1994 | Jommi et al. | 548/239 |
| 5,336,664 | A | 8/1994 | Camaggi et al. | 504/261 |
| 5,352,832 | A * | 10/1994 | Wu et al. | 564/212 |
| 5,382,673 | A | 1/1995 | Clark et al. | 548/239 |
| 5,401,852 | A | 3/1995 | Villa et al. | 548/215 |
| 5,556,829 | A | 9/1996 | Camaggi et al. | 504/199 |
| 5,567,844 | A | 10/1996 | Jommi et al. | 564/209 |
| 5,663,361 | A * | 9/1997 | Towson et al. | 548/233 |
| 5,789,599 | A | 8/1998 | Davis et al. | 548/965 |
| 5,908,937 | A | 6/1999 | Jommi et al. | 548/232 |

FOREIGN PATENT DOCUMENTS

| | | |
|---|---|---|
| CN | 1326926 | 12/2001 |
| EP | 0 014 437 B1 | 2/1983 |
| EP | 0 130 633 A2 | 1/1985 |
| EP | 0 200 739 B1 | 7/1989 |
| EP | 0 423 705 A3 | 4/1991 |
| EP | 0 454 067 A1 | 4/1991 |
| EP | 500 177 A1 | 8/1992 |
| EP | 0 423 705 B1 | 1/1995 |
| EP | 0 130 633 B1 | 9/1996 |
| EP | 500 177 B1 | 1/1999 |
| GB | 745900 | 3/1956 |
| GB | 746015 | 3/1956 |
| GB | 746016 | 3/1956 |
| WO | WO 86/01799 | 3/1986 |
| WO | WO 90/02739 | 3/1990 |
| WO | WO 92/07824 | 5/1992 |
| WO | WO 94/14764 | 7/1994 |
| WO | WO 95/30672 | 11/1995 |
| WO | WO 2003/093221 | 11/2003 |

OTHER PUBLICATIONS

Clark, J. E., "An Enzymatic Route to Florfenicol," *Synthesis*, pp. 891-894, Oct. 1991.

Jommi, G. et al., "2-Oxazolidinones as regioselective protection of β-amino alcohols in the synthesis of 2-amino-1-aryl-3-fluoro-1-propanols," *Gazzetta Chemica Italiana*, vol. 116, pp. 485-489 (1986).

Jommi, G. et al., "Preparation of 2-[4-methlysulfonyl)phenyl]-2,3, Dihydrooxazolo [2,3-α] Isoindol-5(9bH)-One Derivatives and a New Synthesis of Thiamphenicol Analogs," *Gazzetta Chemica Italiana*, vol. 115, pp. 653-658 (1985).

Schumacher, D. et al., "An efficient synthesis of florfenicol," *J Org Chem*., vol. 55, pp. 5291-5294 (1990).

Tyson, R., "Custom Synthesis and Process Development," *Chem. Ind.*, vol. 4, pp. 118-122 (1990).

* cited by examiner

*Primary Examiner*—Golam M. M. Shameem
(74) *Attorney, Agent, or Firm*—Winston & Strawn LLP

(57) ABSTRACT

The present invention is directed to a new process of preparing highly pure Florfenicol. The invention is further directed to new oxazolidine derivatives useful in making Florfenicol and processes of making these derivatives. Examples of such intermediates include (4R,5R)-3-acetyl-2,2-dimethyl-4-hydroxymethyl-5-[4-(methylsulfonyl)phenyl]-1,3-oxazolidine; and (4S,5R)-3-acetyl-2,2-dimethyl-4-fluoromethyl-5-[4-(methylsulfonyl)phenyl]-1,3-oxazolidine.

21 Claims, No Drawings

PROCESS FOR PREPARING FLORFENICOL

CROSS-REFERENCE TO RELATED APPLICATIONS

This application claims priority to India Application No. 806/CHE/2003 filed Oct. 6, 2003.

TECHNICAL FIELD

The present invention relates generally to a new process for preparing Florfenicol and Florfenicol analogs. The invention further relates to new oxazolidine compounds useful in making Florfenicol and processes of making them.

BACKGROUND OF THE INVENTION

Florfenicol, the fluoro derivative of thiamphenicol, has the structure of Formula I.

Formula I

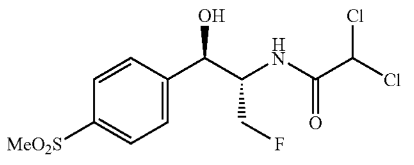

Florfenicol is a broad-spectrum antibiotic compound possessing activity against many Gram negative, Gram positive, and thiamphenicol-resistant microorganisms. Florfenicol, chemically known as (1R,2S)-2-dichloroacetamido-3-fluoro-1-[4-(methylsulfonyl)phenyl]-1-propanol, is of interest as a veterinary product.

U.S. Pat. No. 4,235,892 (hereafter referred to as the “the ’892 patent”) describes a process of converting thiamphenicol into Florfenicol and other analogs. The process disclosed in the ’892 patent includes, for example, protection of the amino group of the amino-diol hydrochloride with a phthalic anhydride to produce a phthalimido-diol. This compound is then fluorinated to produce a phthalimido-fluoro alcohol. Removal of the protecting group with hydrazine hydrate to give a fluoro amine, which is then acylated with methyl dichloroacetate to obtain Florfenicol.

A major drawback to the process disclosed in the ’892 patent is poor fluorination resulting in low production of Florfenicol and low purity. The fluorination step taught by the ’892 patent is accomplished with diethylamine sulfurtrifluoride (DAST), which is expensive and hazardous to use and results in a mixture of fluorinated products. As a result, the process disclosed in the ’892 patent requires further processing using of column chromatography to obtain sufficiently pure product.

An alternate approach to the fluorination step of the ’892 patent is described in U.S. Pat. No. 4,876,352 (hereafter referred to as the “the ’352 patent”). The ’352 patent discloses the preparation of various fluoro oxazoline and oxazolidinone intermediates. The process starts from an oxazoline or oxazolidinone compound, for example, (4R, 5R)-4-hydroxymethyl-5-[4-(methylsulfonyl)phenyl]-2-phenyl-2-oxazoline of Formula II.

Formula II

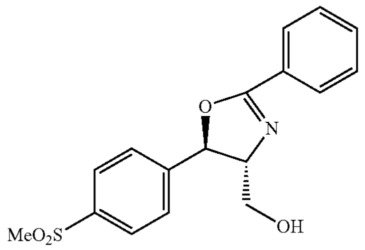

The oxazoline intermediate used in the ’352 patent can be prepared by simultaneously protecting the secondary hydroxyl group and the primary amino group present in (1R,2R)-2-amino-1-[(4-methylsulfonyl)phenyl]-1,3-propanediol of Formula III as described in U.S. Pat. No. 5,227,494.

Formula III

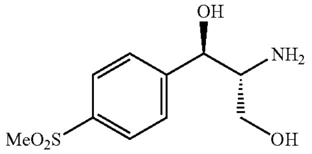

This preparation requires use of toxic benzonitrile and harsh reaction conditions, such as, 18 hours of heating to 115° C. Alternatively, the desired oxazoline can be prepared as disclosed in U.S. Pat. No. 4,743,700 using ethyl benzimidate hydrochloride. The yield of the desired oxazoline product obtained using this process is low, however, with much of the remainder being isomeric oxazoline of Formula IV.

Formula IV

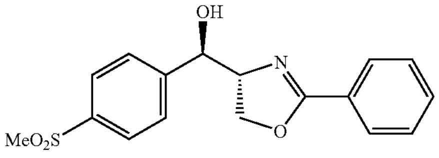

The oxazoline compounds (such as Formula II) can be converted, according to the ’352 patent, to the corresponding fluoro oxazoline of Formula V, for example, by reacting with an Ishikawa reagent, (1,1,2,3,3,3-hexafluoropropyl)diethylamine under pressure.

Formula V

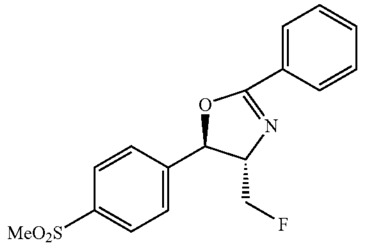

U.S. Pat. No. 5,567,844 discloses that after performance of fluorination step, such as disclosed in the ’352 patent, the fluoro oxazoline intermediates can then be hydrolyzed to obtain an amine of Formula VI.

Formula VI

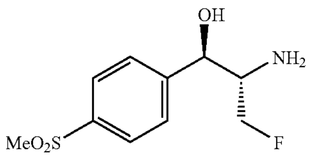

This removal of the oxazoline protecting group requires heating at 100° C. for 18 hours with 12N hydrochloric acid and results in significant amount of by-product, the 1,3-propanediol of Formula III.

The inventors have now surprisingly found a new process of preparing Florfenicol, and analogs thereof, utilizing N-acetylated oxazolidine intermediates, which results in greater efficiency of the hydrolysis of N-acetyl oxazolidine than the prior art processes and higher product purity.

SUMMARY OF THE INVENTION

In view of the prior art described above, the present invention teaches a new process for preparing a compound of Formula VII Formula VII

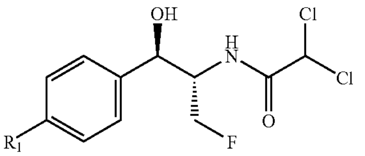

wherein $R_1$ is a methylthio, methylsulfoxy, methylsulfonyl or nitro group. Preferably the product of the new process is Florfenicol of Formula I.

Formula I

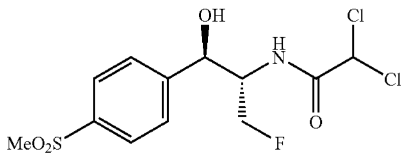

The new process preferably comprises the steps of:

reacting the compound of Formula VIII

Formula VIII

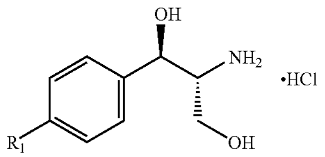

with an agent in the presence of a first organic base and a first organic solvent to produce a compound of Formula IX Formula IX

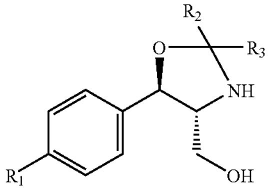

wherein $R_1$ is a methylthio, methylsulfoxy, methylsulfonyl or nitro group; $R_2$ is an alkyl, haloalkyl, cycloalkyl, alkenyl, alkynyl, alkoxy, aralkyl, aralkenyl, aryl or aromatic heterocyclic group; and $R_3$ is a hydrogen, alkyl, haloalkyl, cycloalkyl, alkenyl, alkynyl, alkoxy, aralkyl, aralkenyl, aryl or aromatic heterocyclic group;

converting the compound of Formula IX to a compound of Formula X

Formula X

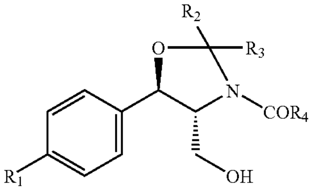

wherein $R_4$ is a hydrogen, alkyl, haloalkyl, cycloalkyl, phenyl or phenylalkyl group, where the phenyl ring may be substituted by one or two halogen, alkyl, alkoxy or nitro groups, by reacting the compound of Formula IX with $R_4COCl$ in the presence of a second organic base in a second organic solvent to produce the compound of Formula X;

fluorinating the compound of Formula X with a fluorinating agent in the presence of a third organic solvent to obtain the compound of Formula XI Formula XI

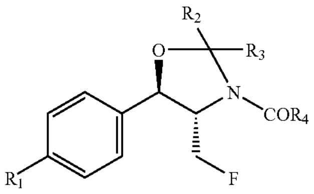

and further processing the compound of Formula XI to obtain the compound of Formula VII.

In a preferred embodiment of the invention, the compound of Formula XI is further processed to obtain the compound of Formula VII by first hydrolyzing the fluoro oxazolidine of Formula XI with an acid to obtain the compound of Formula XII Formula XII

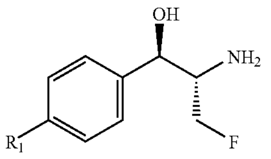

and N-acylating the compound of Formula XII with dichloroacetic acid or a reactive derivative thereof, such as methyl dichloroacetate, ethyl dichloroacetate, dichloroacetyl chloride, to obtain the compound of Formula VII.

The present invention is also directed to new oxazolidine compounds and processes of making them. The inventors surprisingly discovered that the new oxazolidine compounds are extremely useful in producing highly pure Florfenicol or Florfenicol analogs. The oxazolidine compounds of the present invention include the compounds of Formula X Formula X

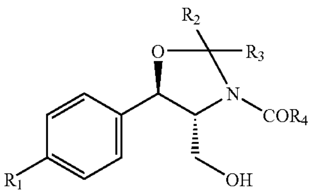

and Formula XI

Formula XI

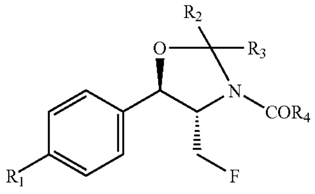

wherein $R_1$, $R_2$, $R_3$ and $R_4$ are as defined above.

Specific non-limiting examples of preferred oxazolidine compounds include (4R,5R)-3-acetyl-2,2-dimethyl-4-hydroxymethyl-5-[4-(methylsulfonyl)phenyl]-1,3-oxazolidine, the compound of Formula XIII Formula XIII

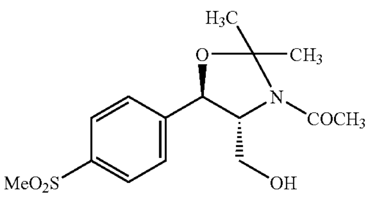

and (4S,5R)-3-acetyl-2,2-dimethyl-4-fluoromethyl-5-[4-(methylsulfonyl) phenyl]-1,3-oxazolidine, the compound Formula XIV.

Formula XIV

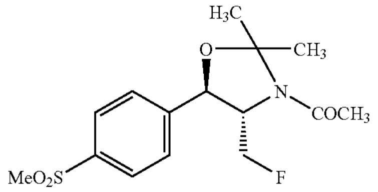

DETAILED DESCRIPTION OF THE PREFERRED EMBODIMENTS

The present invention is directed to a new process of preparing Florfenicol and analogs thereof The term "analogs of Florfenicol," as used herein, includes, without limitation, those analogs which are known to exhibit activity as active antibiotics, for example, compounds wherein the methylsulfonyl of Florfenicol is replaced by a methylthio, methylsulfoxy or nitro group, as well as any other chemical analogs, whether or not currently known to exhibit such activity.

The present invention is also directed to processes of preparing oxazolidine compounds useful in producing highly pure Florfenicol. The inventors surprisingly found that their newly discovered processes, involving these oxazolidine compounds, resulted in greater efficiency than the prior art processes and higher product purity discussed above.

The present invention further encompasses the novel oxazolidine intermediates produced in these processes.

In one embodiment, the present invention is directed to an oxazolidine compound of Formula X and the process of making it.

Formula X

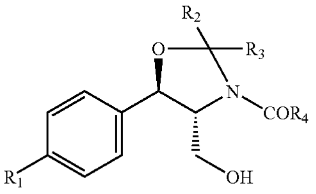

As used throughout this application, (except where otherwise expressly indicated) the functional groups are defined as follows: $R_1$ is a methylthio, methylsulfoxy, methylsulfonyl or nitro group; $R_2$ is an alkyl, haloalkyl, cycloalkyl, alkenyl, alkynyl, alkoxy, aralkyl, aralkenyl, aryl or aromatic heterocyclic group; $R_3$ is a hydrogen, alkyl, haloalkyl, cycloalkyl, alkenyl, alkynyl, alkoxy, aralkyl, aralkenyl, aryl, or aromatic heterocyclic group; and $R_4$ is a hydrogen, alkyl, haloalkyl, cycloalkyl, phenyl or phenylalkyl group, where the phenyl ring may be substituted by one or two halogen, alkyl, alkoxy or nitro groups.

The process of preparing the oxazolidine compound of Formula X involves a two-step process. During step one, the amino diol compound of Formula VIII Formula VIII

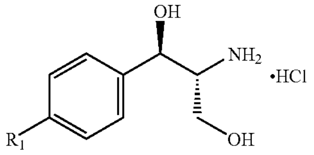

is treated with an agent in the presence of a first organic base and a first organic solvent, resulting in an oxazolidine compound of Formula IX.

Formula IX

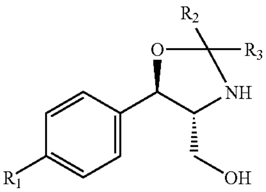

Subsequently during step two, the compound of Formula IX is reacted with $R_4COCl$ in the presence of a second organic base in a second organic solvent to produce the compound of Formula X.

The agent used during step one can be acetone, 2-methoxypropene or 2,2-dimethoxypropane and preferably the agent is acetone.

The first solvent used in step one can be any suitable solvent, preferably acetone, toluene, xylene, hexane or a mixture thereof and most preferably acetone. If acetone is used as the solvent, it can also serve as the agent to react with the compound of Formula VIII to yield the oxazolidine compound of Formula IX.

Furthermore, the second organic solvent used in step two can be any suitable solvent, preferably methylene chloride, chloroform or a mixture thereof and most preferably methylene chloride.

The first or second organic base used in steps one and two of the process can be any suitable organic base. Preferably, however, the base is an alkylamine and more preferably it is triethylamine.

In a preferred embodiment, $R_2$, $R_3$ and $R_4$ in Formulas VIII, IX and X are all alkyl groups and more preferably methyl groups. Specifically, the product produced is preferably the oxazolidine compound of Formula XIII.

Formula XIII

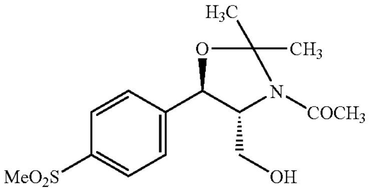

In another preferred embodiment of preparing the compound of Formula X, the compound of Formula VIII is heated in about eight to ten times by volume of acetone to produce the oxazolidine of Formula IX. The reaction is preferably carried out at about 50° C. to about 60° C. in the presence of 1.2 to 2.0 mole of triethylamine. Furthermore, step two of the process is preferably carried out in methylene chloride with acetyl chloride and a triethylamine base to obtain the oxazolidine compound of Formula X in good yield.

The present process has the advantage of being regioselective, involving relatively mild reaction conditions and no racemization of the chiral starting material.

The present invention also teaches a process of preparing a fluoro oxazolidine compound of Formula XI.

Formula XI

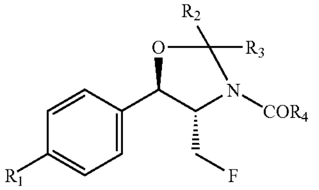

This is achieved by fluorinating the compound of Formula X with a fluorinating agent in the presence of an organic solvent.

Formula X

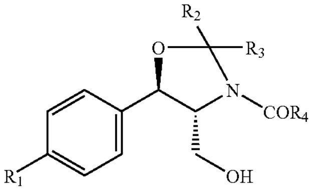

The fluorinating agent used in fluorinating the compound of Formula X can be any suitable fluorinating agent, preferably N-(2-chloro-1,1,2-trifluoroethyl) diethylamine, N-(2-chloro-1,1,2-trifluoroethyl) dimethylamine, N-(2-chloro-1,1,2-trifluoroethyl) dipropylamine, N-(2-chloro-1,1,2-trifluoroethyl) pyrrolidine, N-(2-chloro-1,1,2-trifluoroethyl) 2-methylpyrrolidine, N-(2-chloro-1,1,2-trifluoroethyl)4-methylpiperazine, N-(2-chloro-1,1,2-trifluoroethyl)morpholine, N-(2-chloro-1,1,2-trifluoroethyl) piperidine, or N-(1,1,2,3,3,3-hexafluoropropyl)diethylamine; and more preferably N-(1,1,2,3,3,3-hexafluoropropyl) diethylamine.

In a preferred embodiment, the molar ratio of N-(1,1,2,3,3,3-hexafluoropropyl) diethylamine to the compound of Formula X is between 1:1 and 3:1 and more preferably about 2:1. The organic solvent used in the fluorinating step include acetonitrile, ethyl acetate, chlorinated hydrocarbon such as methylene chloride, chloroform, chlorobenzene and the like. A preferred solvent is methylene chloride. The fluorination preferably is carried out at a temperature of about 80° C. to 110° C. and also at a pressure of at least about 60 psi. Generally the pressure should not exceed 100 psi for manufacturing convenience.

In another preferred embodiment $R_2$, $R_3$ and $R_4$ in Formulas X and XI are all alkyl groups and more preferably methyl groups. Specifically, the compound produced by the fluorination process is preferably the oxazolidine compound of Formula XIV.

Formula XIV

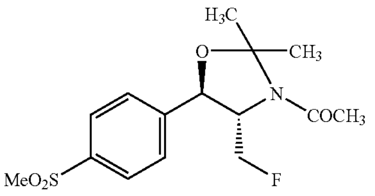

The present invention is further directed to a novel process of preparing a compound of Formula VII.

Formula VII

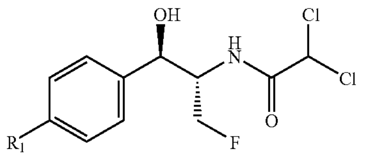

The process typically comprises the steps of:

producing an N-acylated oxazolidine derivative of Formula X using the two-step process fully described above;

fluorinating the compound of Formula X to obtain the fluoro oxazolidine compound of Formula XI using the fluorinating process also fully described above; and further processing the compound of Formula XI to obtain the compound of Formula VII.

The processing of the compound of Formula XI preferably comprises the steps of hydrolyzing the compound of Formula XI with an acid to obtain the compound of Formula XII Formula XII

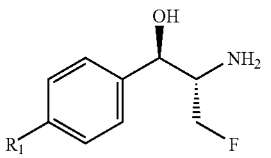

and N-acylating the compound of Formula XII with dichloroacetic acid or a reactive derivative thereof such as methyl dichloroacetate, ethyl dichloroacetate, dichloroacetyl chloride to obtain the compound of Formula VII.

The protective groups from the compound of Formula XI are removed by treatment with an inorganic acid and most preferably aqueous hydrochloric acid.

In a preferred embodiment, the processing of the fluoro oxazolidine compound of Formula XI is accomplished by removing the protective groups to obtain the amine of Formula XII. The protective groups are removed using 6N aqueous hydrochloric acid at about 90° C. to 100° C. for about at least 30 minutes.

The following non-limiting example is a preferred embodiment of the inventive process. In this embodiment, Florfenicol of Formula I Formula I

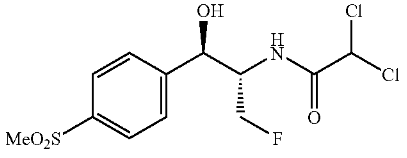

is produced by the process comprising the steps of:

converting a compound of Formula XV

Formula XV

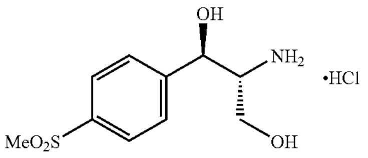

into an oxazolidine derivative of Formula XVI

Formula XVI

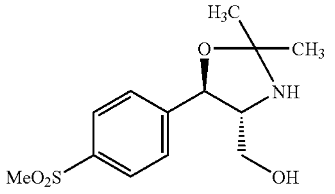

acylating the compound of Formula XVI to obtain the N-acylated oxazolidine derivative of Formula XIII Formula XIII

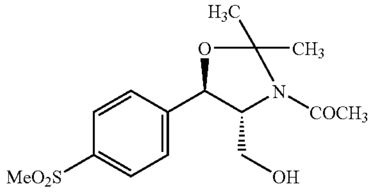

fluorinating the compound of Formula XIII to obtain the corresponding fluoro oxazolidine of Formula XIV Formula XIV

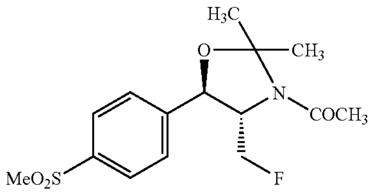

hydrolyzing the fluoro oxazolidine of Formula XIV to amine of Formula VI

Formula VI

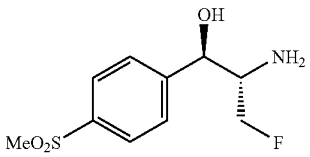

and N-acylation of the amine of Formula VI to obtain Florfenicol.

In this particular embodiment the compound of Formula XVI is obtained by reacting the compound of Formula XV with acetone at 50° C. to 60° C. in presence of triethylamine. The compound of Formula XVI is acylated with acetyl chloride and the fluorination of the compound of Formula XIII is carried out using (1,1,2,3,3,3-hexafluoropropyl)diethylamine in methylene chloride at 80° C. to 110° C. at a pressure of 60 psi to 100 psi. The fluoro oxazolidine of Formula XIV is then hydrolyzed using an aqueous hydrochloric acid at a temperature of about 90° C. to 100° C., followed by N-acylating the compound of Formula VI using dichloroacetic acid, or a reactive derivative thereof, in the presence of triethylamine to produce Florfenicol of Formula I.

Although preferred embodiments of the invention are described in the foregoing description, it is understood that the invention is not limited to the specific embodiments disclosed herein but is capable of numerous modifications by one of ordinary skill in the art.

EXAMPLES

The new process of synthesizing Florfenicol is illustrated by the following examples. These examples, are for illustrative purposes only, and are not to be construed as limiting the appended claims.

Example 1

Preparation of (1R,2S)-2-DICHLOROACETAMIDO-3-FLUORO-1-[4-(METHYLSULFONYL) PHENYL]-1-PROPANOL(FLORFENICOL)

STEP-I. Preparation of (4R,5R)-3-Acetyl-2,2-Dimethyl-4-Hydroxymethyl-5-[4 (Methylsulfonyl)Phenyl]-1,3-Oxazolidine(N-Acetyl Oxazolidine)

A suspension of (1R,2R)-2-amino-1-[4-(methylsulfonyl) phenyl]-1,3-propanediol hydrochloride (50 g, 0.178 mole), triethylamine (35.88 g, 0.355 mole) and acetone (400 ml) were heated at 50° C. to 60° C. for 12 hours. The reaction mass was cooled to room temperature, filtered and the filtrate was evaporated under reduced pressure at 40° C. to 45° C. The mass was dissolved in methylene chloride (450 ml) and to this solution triethylamine (26.91 g, 0.266 mole) and acetyl chloride (15.34 g, 0.195 mole) were added at 10° C. to 15° C. in an inert atmosphere. After completion of the reaction, the reaction mass was washed with 10% w/v aqueous ammonium chloride solution (100 ml) and the organic layer was evaporated to dryness. The residue was dissolved in methanol (150 ml) and stirred with potassium carbonate (9.8 g, 0.071 mole) for 30–35 minutes at 20° C. to 25° C. The solvent was evaporated and the reaction mass was dissolved in methylene chloride (125 ml) and washed with water (25 ml). The organic layer was concentrated under reduced pressure to obtain viscous oil, which was crystallized from ethyl acetate (100 ml) to obtain the title compound (42.5 g, HPLC purity: 96.0%).

The various parameters of the end product were determined to be the following:

Melting Range: 108°–115° C.;

Specific Optical Rotation: $[\alpha]^{25}_{D}$:+27.5° (C=0.5, Methanol)

$^1$H NMR (300 MHz) in DMSO-$d_6$: δ(ppm); 1.52 (s, 3H, $CH_3$), 1.54 (s, 3H, $CH_3$), 2.06 (s, 3H, $CH_3$), 3.23 (s, 3H, $CH_3$), 3.66 (brm, 2H, $CH_2$), 4.15 (brs, 1H, H-4), 5.23 (d, J=3.3 Hz, 1H, H-5), 5.33 (t, J=5.4 Hz, 1H, OH), 7.73 (d, J=8.4 Hz, 2H, ArH); 7.95 (d, J=8.4 Hz, 2H, ArH).

Mass: m/z; 328 [$(MH)^+$]

STEP-II: Preparation of (4S,5R)-3-Acetyl-2,2-Dimethyl-4-Fluoromethyl-5-[4 (Methylsulfonyl)Phenyl]-1,3-Oxazolidine(Fluoro Oxazolidine)

To a suspension of (4R,5R)-3-acetyl-2,2-dimethyl-4-hydroxymethyl-5-[(4-methylsulfonyl)phenyl]-1,3-oxazolidine (25 g, 0.076 moles) in methylene chloride (250 ml) under nitrogen atmosphere, was added (1,1,2,3,3,3-hexafluoropropyl)diethylamine (Ishikawa reagent, 34 g, 0.152 moles) in a closed reactor. The reactor was heated at 90° C. to 100° C. at 90 psi to 100 psi for 1 hour. The reaction mass was cooled to 0° C., washed with saturated sodium chloride solution (50 ml) and used as such in the next step.

STEP-III: Preparation of (b 1R,2S)-1-[4-(Methylsulfonyl) Phenyl]-2-Amino-3-Fluoro-1-Propanol (Fluoro Amine)

The organic solution (~275 ml, as obtained above) was added to 6N aqueous hydrochloric acid (250 ml) at 90° C. to 100° C. over a period of 30 min. Methylene chloride was distilled simultaneously from the reaction mixture. After stirring at 90–100° C. for another 30 min, the solution was cooled to room temperature and washed with dichloroethane (3×50 ml). The pH of the aqueous layer was adjusted to 12.0 at 5° C. to 10° C. with 50% w/v sodium hydroxide solution and extracted with methylene chloride (300 ml). The methylene chloride layer was concentrated to obtain the title compound as a residual solid (15 g, HPLC purity: 98.0%). Analytical sample was prepared by crystallization from isopropyl alcohol.

The various parameters of the end product were determined to be the following:

Melting Range: 99°–103° C.

Specific Optical Rotation: $[\alpha]^{26}_{D}$: −35.2° (C=0.5, Methanol)

$^1$H NMR (300 MHz) in DMSO-$d_6$: δ(ppm); 1.56 (brs, 2H, $NH_2$), 2.97–3.05 (m, 1H, H-2), 3.2 (s, 3H, $CH_3$), 4.10–4.49 (m, 2H, $CH_2$, H-3), 4.71 (d, J=3.3 Hz, 1H, H-1), 5.7 (brs, 1H, OH), 7.62 (d, J=8.1 Hz, 2H, ArH), 7.95 (d, J=8.1 Hz, 2H, ArH).

Mass: m/z; 248 [$(MH)^+$]

STEP-IV: Preparation of (1R,2S)-2-Dichloroacetamido-3-Fluoro-1-[4-(Methylsulfonyl)Phenyl]-1-Propanol (Florfenicol)

To a solution of (1R,2S)-1-[4-(methylsulfonyl)phenyl]-2-amino-3-fluoro-1-propanol (5 g, 0.02 moles) in methanol (50 ml) was added methyl dichloroacetate (14.5 g; 0.10 g) and triethylamine (2.05 g, 0.02 mole) and stirred at room temperature for 18 hours. After completion of reaction, methanol was distilled off from the reaction mass, toluene (25 ml) and water (5 ml) were added. The product thus precipitated was filtered, washed with methylene chloride (20 ml) and crystallized from 2-propanol/water (5:1) to give 5 g of title compound having purity 99.20% by HPLC.

The various parameters of the end product were determined to be the following:

Melting Range: 153°–154° C.

Specific Optical Rotation: $[\alpha]^{20}_{D}$: −18.2° (C=0.5, N,N-dimethylformamide)

$^1$H NMR (300 MHz) in DMSO-$d_6$: δ(ppm); 3.17 (s, 3H, $CH_3$), 4.29–4.76 [m, 3H, H-2 and H-3($CH_2$)], 4.99 (brs, 1H, H-1), 6.16 (d, J=2.7 Hz, OH), 6.46 (s, 1H, $CHCl_2$), 7.62 (d, J=6.9 Hz, 2H, ArH), 7.86 (d, J=6.9 Hz, 2H, ArH), 8.62 (d, J=8.4 Hz, NH).

Mass: m/z; 358 [$(MH)^+$], 360 [$(MH+2)^+$], 362 [$(MH+4)^+$]

Example 2

Preparation of (4R,5R)-3-ACETYL-2,2-DIMETHYL-4-HYDROXYMETHYL-5-[4-(METHYLSULFONYL)PHENYL]-1,3-OXAZOLIDINE(N-ACETYL OXAZOLIDINE)

A suspension of (1R,2R)-2-amino-1-[4-(methylsulfonyl)phenyl]-1,3-propanediol hydrochloride (50 g, 0.178 mole), triethylamine (35.88 g, 0.355 mole), acetone (250 ml) and toluene (250 ml) were heated at 70–80° C. for 18 hours. The reaction mass was cooled to room temperature, filtered and the filtrate was evaporated under reduced pressure at 40° C. to 45° C. The mass was dissolved in methylene chloride (450 ml) and to this solution triethylamine (26.91 g, 0.266 mole) and acetyl chloride (15.34 g, 0.195 mole) were added at 10° C. to 15° C. in an inert atmosphere. After completion of the reaction, the reaction mass was washed with 10% w/v aqueous ammonium chloride solution (100 ml) and the organic layer was evaporated to dryness. The residue was dissolved in methanol (150 ml) and stirred with potassium carbonate (9.8 g, 0.071 mole) for 30–35 minutes at 20° C. to 25° C. The solvent was evaporated and the reaction mass was dissolved in methylene chloride (125 ml) and washed with water (25 ml). The organic layer was concentrated under reduced pressure to obtain viscous oil, which was crystallized from ethyl acetate (100 ml) to obtain the title compound (40 g, HPLC purity: 97.3%).

Example 3

Preoaration of (4S,5R)-3-ACETYL-2,2-DIMETHYL-4-FLUOROMETHYL-5-[4 (METHYLSULFONYL)PHENYL]-1,3-OXAZOLIDINE (FLUORO OXAZOLIDINE)

To a suspension of (4R,5R)-3-acetyl-2,2-dimethyl-4-hydroxymethyl-5-[(4-methylsulfonyl)phenyl]-1,3-oxazolidine (10 g, 0.031 moles) in acetonitrile (120 ml) under nitrogen atmosphere, was added (1,1,2,3,3,3-hexafluoropropyl)diethylamine (Ishikawa reagent, 13.65 g, 0.061 moles) in a closed reactor. The reactor was heated at 90° C. to 100° C. for 3 hours. The reaction mass was cooled to room temperature and concentrated under reduced pressure distillation at 40–45° C. to obtain an oily residue. The residue was dissolved in methylene chloride (100 ml), washed with saturated sodium chloride (20 ml) and used as such in the next step.

Example 4

Preparation of (1R,2S)-2-DICHLOROACETAMIDO-3-FLUORO-1-[4-(METHYLSULFONYL)PHENYL]-1-PROPANOL (FLORFENICOL)

To a solution of (1R,2S)-1-[4-(methylsulfonyl)phenyl]-2-amino-3-fluoro-1-propanol (5 g, 0.02 moles) in methanol (50 ml) was added methyl dichloroacetate (14.5 g; 0.10 g) and heated to reflux at 60° C. to 65° C. for 18 hours. After completion of reaction, methanol was distilled off from reaction mass, toluene (25 ml) and water (5 ml) were added. The product thus precipitated was filtered, washed with methylene chloride (20 ml) and crystallized from 2-propanol/water (5:1) to give 5 g of Florfenicol with 99% HPLC purity.

Example 5

Preparation of (1R,2S)-2-DICHLOROACETAMIDO-3-FLUORO-1-[4-(METHYLSULFONYL)PHENYL]-1-PROPANOL (FLORFENICOL)

To a solution of (1R,2S)-1-[4-(methylsulfonyl)phenyl]-2-amino-3-fluoro-1-propanol (5 g, 0.02 moles) in methylene chloride (100 ml) triethylamine (3.0 g, 0.03 mole) and dichloro acetyl chloride (3.6 g; 0.025 mole) were added at 10–15° C. After completion of reaction in 30 minutes, water (10 ml) was added and layers were separated. Solvent was distilled off from reaction mass, toluene (25 ml) and water (5 ml) were added. The product thus precipitated was filtered, washed with methylene chloride (20 ml) and crystallized from ethanol/water (4:1) to give 5 g of the title compound with purity 99.5% by HPLC.

Any and all publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A process of preparing a compound of Formula VII:

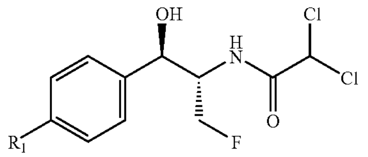

wherein $R_1$ is a methylthio, methylsulfoxy, methylsulfonyl or nitro group, the process comprising the steps of:

reacting the compound of Formula VIII

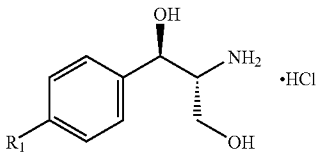

with an agent in the presence of a first organic base and a first organic solvent to produce a compound of Formula IX

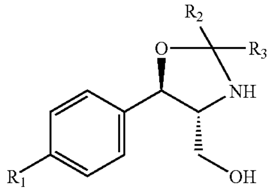

wherein $R_2$ is an alkyl, haloalkyl, cycloalkyl, alkenyl, alkynyl, alkoxy, aralkyl, aralkenyl, aryl or aromatic heterocyclic group; and $R_3$ is a hydrogen, alkyl, haloalkyl, cycloalkyl, alkenyl, alkynyl, alkoxy, aralkyl, aralkenyl, aryl or aromatic heterocyclic group;

converting the compound of Formula IX to a compound of Formula X:

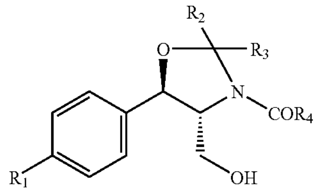

wherein $R_4$ is a hydrogen, alkyl, haloalkyl, cycloalkyl, phenyl or phenylalkyl group, where the phenyl ring may be substituted by one or two halogen, alkyl, alkoxy or nitro groups, by reacting the compound of Formula IX with $R_4COCl$ in the presence of a second organic base in a second organic solvent to produce the compound of Formula X;

fluorinating the compound of Formula X with a fluorinating agent in the presence of a third organic solvent to obtain the compound of Formula XI and

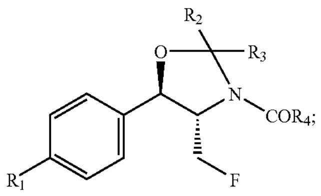

further processing the compound of Formula XI to obtain the compound of Formula VII.

2. The process of claim 1, wherein the processing of the compound of Formula XI comprises hydrolyzing the compound of Formula XI with an acid to obtain the compound of Formula XII

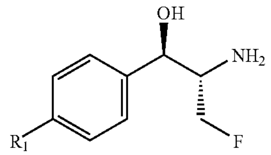

and

N-acylating the compound of Formula XII with dichloroacetic acid or a reactive derivative thereof to obtain the compound of Formula VII.

3. The process according to claim 1, wherein the agent is acetone, 2-methoxypropene or 2,2-dimethoxypropane.

4. The process according to claim 3, wherein the agent is acetone.

5. The process according to claim 4, wherein the compound of Formula VIII is heated in about eight to ten times by volume of acetone.

6. The process according to claim 1, wherein the first organic solvent is acetone, toluene, xylene, hexane or a mixture thereof.

7. The process according to claim 1, wherein at least either the first or second organic base is an alkylamine.

8. The process according to claim 7, wherein the alkylamine is triethylamine.

9. The process according to claim 1, wherein in the compound of Formula IX is obtained by reacting the compound of Formula VIII with acetone at a temperature of about 50° C. to about 60° C. in the presence of an alkylamine.

10. The process according to claim 1, wherein the fluorinating agent is N-(2-chloro-1,1,2-trifluoroethyl) diethylamine, N-(2-chloro-1,1,2-trifluoroethyl) dimethylamine, N-(2-chloro-1,1,2-trifluoroethyl) dipropylamine, N-(2-chloro-1,1,2-trifluoroethyl) pyrrolidine, N-(2-chloro-1,1,2-trifluoroethyl) 2-methylpyrrolidine, N-(2-chloro-1,1,2-trifluoroethyl) 4-methylpiperazine, N-(2-chloro-1,1,2-trifluoroethyl) morpholine, N-(2-chloro-1,1,2-trifluoroethyl) piperidine, or N-(1,1,2,3,3,3-hexafluoropropyl) diethylamine.

11. The process according to claim 10, wherein the fluorinating step of the compound of Formula X is carried out using (1,1,2,3,3,3-hexafluoropropyl) diethylamine.

12. The process according to claim 11, wherein the molar ratio of N-(1,1,2,3,3,3-hexafluoropropyl) diethylamine to the compound of Formula X is between 1:1 and 3:1.

13. The process according to claim 12, wherein the molar ratio of N-(1,1,2,3,3,3-hexafluoropropyl) diethylamine to the compound of Formula X is about 2:1.

14. The process according to claim 1, wherein the fluorinating step is carried out at a temperature of about 80° C. to about 110° C. and at a pressure of about at least 60 psi.

15. The process according to claim 1, wherein the second or third organic solvent is acetonitrile, ethyl acetate, methylene chloride, chloroform, chlorobenzene, or another chlorinated hydrocarbon.

16. The process according to claim 15, wherein the second or third organic solvent is methylene chloride.

17. The process according to claim 2, wherein the acid is an inorganic acid.

18. The process according to claim 17, wherein the acid is aqueous hydrochloric acid.

19. The process according to claim 18, wherein the hydrolyzing step is carried out by heating the compound of Formula XI with 6N aqueous hydrochloric acid at a temperature of about 90° C. to about 100° C. for about 30 minutes.

20. The process according to claim 1, wherein $R_2$, $R_3$ and $R_4$ are all alkyls.

21. The process according to claim 1, wherein $R_2$, $R_3$ and $R_4$ are all methyl groups.

* * * * *

UNITED STATES PATENT AND TRADEMARK OFFICE

CERTIFICATE OF CORRECTION

PATENT NO. : 7,126,005 B2
APPLICATION NO. : 10/735892
DATED : October 24, 2006
INVENTOR(S) : Handa et al.

It is certified that error appears in the above-identified patent and that said Letters Patent is hereby corrected as shown below:

Column 15

Lines 54-65, after "to obtain the compound of Formula XI", delete "and;" and replace the structure on lines 56-63 with the following:

--

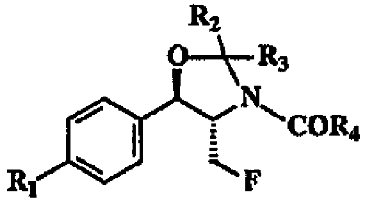

; and --

Signed and Sealed this

Second Day of January, 2007

JON W. DUDAS

*Director of the United States Patent and Trademark Office*